United States Patent [19]
Harding

[11] Patent Number: 5,394,453
[45] Date of Patent: Feb. 28, 1995

[54] DEVICE FOR MEASURING THE PULSE TRANSFER SPECTRUM OF ELASTICALLY SCATTERED X-RAY QUANTA

[75] Inventor: Geoffrey Harding, Hamburg, Germany

[73] Assignee: U.S. Philips Corporation, New York, N.Y.

[21] Appl. No.: 15,096

[22] Filed: Feb. 5, 1993

[30] Foreign Application Priority Data

Feb. 6, 1992 [DE] Germany .............. 4203354
Jul. 7, 1992 [DE] Germany .............. 4222227

[51] Int. Cl.⁶ .................................. G01N 23/201
[52] U.S. Cl. ........................ 378/86; 378/87; 378/88; 378/149
[58] Field of Search ............ 378/86, 87, 88, 89, 378/147, 149, 154

[56] References Cited

U.S. PATENT DOCUMENTS

| | | | |
|---|---|---|---|
| 3,197,638 | 7/1965 | Sinclair | 378/86 |
| 4,951,305 | 8/1990 | Moore et al. | 378/154 X |
| 5,007,072 | 4/1991 | Jenkins et al. | |
| 5,008,911 | 4/1991 | Harding | 378/86 |

FOREIGN PATENT DOCUMENTS 0370347 5/1990 European Pat. Off. .
0462658 12/1991 European Pat. Off. .

Primary Examiner—David P. Porta
Attorney, Agent, or Firm—Jack D. Slobod

[57] ABSTRACT

A device for measuring the pulse transfer spectrum of X-ray quanta, includes a polychromatic X-ray source and an energy-resolving detector device for the scattered-X-ray quanta. A secondary diaphragm device, arranged between the examination zone in which the object whose pulse transfer spectrum is to be determined is situated, and the detector device ensure on the one that each detector element of the detector device can detect scattered radiation only at a comparatively accurately defined scatter angle, and that the scatter angles of the various detector elements do not excessively deviate from one another.

12 Claims, 5 Drawing Sheets

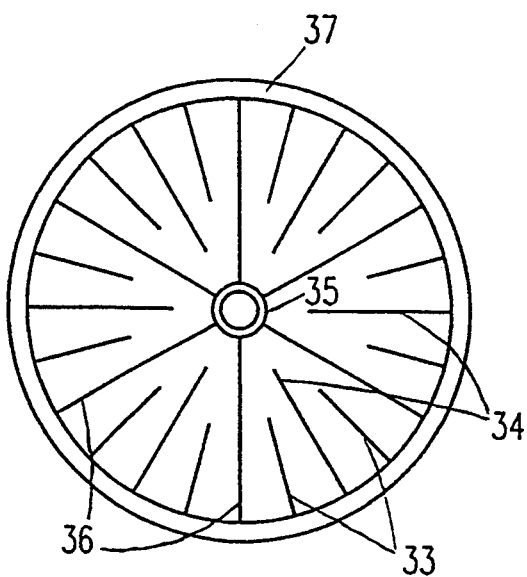
Fig.2
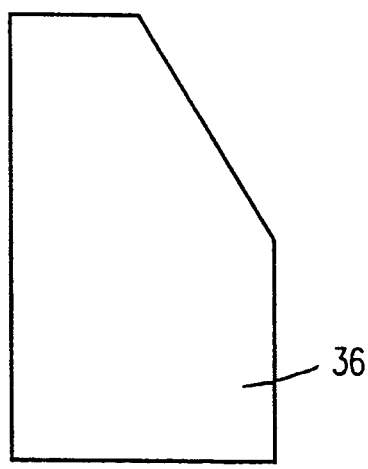 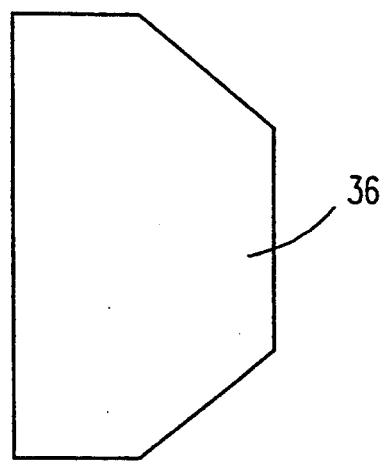
Fig.6a  Fig.6b

DEVICE FOR MEASURING THE PULSE TRANSFER SPECTRUM OF ELASTICALLY SCATTERED X-RAY QUANTA

BACKGROUND OF THE INVENTION

1. Field of the Invention

The invention relates to a device for measuring the pulse transfer spectrum of elastically scattered X-ray quanta, including a polychromatic X-ray source, a primary diaphragm device which is arranged between the X-ray source and the examination zone and which serves to form a primary beam irradiating the examination zone as a surface of cone, a detector device having a plurality of detector elements for detecting X-ray quanta scattered in the examination zone, and a secondary diaphragm device which is arranged between the examination zone and the detector device and which has imaging slits which enclose, as an arc of circle, a system axis extending through the X-ray source.

2. Description of the Related Art

A device of this kind is known from EP-OS 462 658 which corresponds to commonly-owned U.S. Pat. No. 5,231,652 and can be used, for example for the identification, on the basis of their pulse transfer spectrum, of substances present in a piece of luggage, notably crystalline substances (explosives). The secondary diaphragm device thereof is formed by a plate provided with an annular slit. The examination zone is imaged on the detector device through said slit; therefore, such a slit will also be referred to hereinafter as an imaging slit. The likewise annular detector elements are capable of detecting the scattered radiation through the imaging slit, said scattered radiation being generated within the examination zone by the primary beam. The scattered radiation from the part of the examination zone nearest to the system axis is detected by the detector element situated furthest from the system axis, whereas the scattered radiation from the part situated furthest from the system axis is detected by the detector element situated nearest to the system axis. Even though each detector element detects the scattered radiation emanating from the primary beam at a defined scatter angle, the scatter angles associated with the various detector elements deviate from one another.

Because the pulse transfer is proportional to the product of the sine of half the scatter angle and the energy of the elastically scattered X-ray quantum, the ratio of the maximum energy to the minimum energy of the X-ray quanta emitted by the X-ray source must be substantially greater than the ratio of the maximum pulse transfer to the minimum pulse transfer to be measured by each of the detector elements. When the ratio of the maximum pulse transfer to the minimum pulse transfer is, for example 1.8:0.8 (i.e. 2.25:1), a larger ratio of highest to lowest energy of the X-ray quanta used for determining the pulse transfer is required. Depending on the difference in scatter angle, this ratio may be, for example 4:1. This may give rise to problems, because X-ray quanta of low energy are strongly absorbed in the examination zone, whereas X-ray quanta of higher energy are not sufficiently absorbed in customary semiconductor detectors (Ge, Li), so that the sensitivity of these detectors decreases for quanta of higher energy.

In this respect the ratios in the devices disclosed in U.S. Pat. No. 5,007,072 as well as in EP-OS 370 347 are more attractive, because all detector elements detect only the X-ray quanta scattered at the same scatter angle. Therefore, the ratio of the maximum to the minimum quantum energy therein need not be greater than the ratio of the maximum to the minimum pulse transfer. However, a very complex secondary diaphragm device is required to ensure that all detector elements can be struck by scattered radiation only at the relevant scatter angle. The secondary diaphragm device should then comprise a number of elongate collimator bodies which are arranged at a small distance from one another. The manufacture of such a secondary diaphragm device, however, is intricate.

SUMMARY OF THE INVENTION

It is the object of the invention to construct a device of the kind set forth so that on the one hand the secondary diaphragm device may be comparatively simple and on the other hand the required energy range of the X-ray quanta can be reduced in comparison with the device disclosed in EP-OS 462 658.

This object is achieved in accordance with the invention in that the device is constructed and the slit-shaped apertures in the secondary diaphragm device are arranged so that each of the apertures can transmit only the scattered radiation from a part of the examination zone to the detector device, the scattered radiation from a respective part of the examination zone situated nearer to the X-ray source being detected by detector elements situated at a smaller distance from the system axis than detector elements detecting scattered radiation from a part of the examination zone which is situated further from the X-ray source, no or hardly any overlap occurring of the parts of the examination zone whose scattered radiation is detected by the detector device via the apertures.

Thus, in accordance with the invention the scattered radiation generated in the examination zone by the primary beam is distributed between several apertures. Therefore, none of these apertures images the entire examination zone on the detector device. The scattered radiation from adjacent parts of the examination zone is incident on the detector elements via neighbouring apertures in the secondary diaphragm device, so that each part of the examination zone irradiated by the primary beam can emit scattered radiation to the detector device only through a respective one of the slit-shaped apertures in the secondary diaphragm device.

Because each time only a part of the examination zone is imaged on the detector device via a slit, the angle at which the edge rays from this part to the detector device intersect one another in the aperture decreases. As a result, the ratio of the maximum to the minimum scatter angle is reduced, so that the range of quantum energy required for a predetermined pulse transfer range is reduced (in comparison with a device as disclosed in EP-OS 462 658).

The various parts of the examination zone should not overlap. However, because the width of the slit-shaped apertures, is not zero, scattered radiation from the edge zone of a part of the examination zone associated with a group of detector elements via a slit will inevitably reach also other detector elements through another slit. This component, however, should be small and amount to less than, for example 5% of the scattered radiation;

the term "non-overlapping" or "only slightly overlapping" should, therefore, be interpreted in this sense.

In an embodiment of the invention, the secondary diaphragm device comprises n imaging slits, n being an integer greater than 2, groups of detector elements receiving via the imaging slits, scattered radiation from adjoining parts of the examination zone, the detector elements of a group and the part of the examination zone associated with these elements via an imaging slit being situated further from the system axis as the radius of curvature of the associated imaging slit is greater. The examination zone is thus subdivided into n parts whose scattered radiation is incident on a respective one of the n groups of detector elements via a respective one of the n slits. This results in a substantial reduction of the scatter angle range and hence of the energy range of the X-ray quanta required for a given pulse transfer range.

In a further embodiment of the invention, the examination zone contains the centre between the X-ray source and the detector device, the centre preferably being situated nearer to the boundary of the examination zone at the detector side than to the boundary thereof at the source side. For given detector dimensions and a given (mean) scatter angle, in this embodiment the smallest distances between X-ray source and detector plane and/or the largest dimensions (diameters) of the primary beam in the examination zone are obtained. The larger the dimensions of the primary beam in the examination zone, the faster an object, for example a piece of luggage, can be examined.

In the simplest case the imaging slits may be provided in a flat diaphragm plate of a radiation-absorbing material. However, the greater the depth of the examination zone in comparison with its distance from the detector plane, the more evident it will become that the individual slits have different imaging scales. The imaging scale corresponds to the quotient of the distance between the detector element and the associated slit and the distance between the part of the examination zone associated with the relevant detector element and the slit. This means that the mean scatter angle of the scattered radiation traversing the individual imaging slits varies from one slit to another. For the reasons explained above, a comparatively large energy range of the X-ray quanta will then be required for a given pulse transfer range.

The imaging scale can be kept constant when the imaging slits are arranged in different planes instead of in one plane, the imaging scale of an imaging slit then being greater as its distance from the detector plane is smaller. In that case the secondary diaphragm device should comprise either a comparatively complex, non-flat diaphragm member or a separate diaphragm plate for each slit.

However, in an embodiment of the invention the secondary diaphragm device comprises at least two flat diaphragm plates which comprise selection slits in addition to imaging slits so that the scattered radiation detected by the individual detector elements traverses an imaging slit and at least one selection slit. The number of diaphragm plates may then be smaller than the number of slits. Each diaphragm plate has a double function in as far as it comprises on the one hand imaging slits and on the other hand the (wider) selection slits which ensure that each detector element can be struck only be scattered radiation from a given part of the examination zone.

In order to ensure that each detector element is struck by scattered radiation only at a comparatively accurately defined angle, it is necessary to suppress scattered radiation enclosing a comparatively large angle relative to the planes containing the system axis. To this end, in a further embodiment of the invention a collimator device comprising laminations for absorbing X-rays is provided between the examination zone and the detector device, the laminations being situated in planes containing the system axis.

In a first version, the laminations may have different dimensions in the direction perpendicular to the system axis, so that the clearance between the laminations varies as little as possible as a function of the distance from the system axis. In a second version, suitable for combination with the foregoing version, the laminations are shorter at their side facing the system axis than at their side which is remote therefrom.

BRIEF DESCRIPTION OF THE DRAWING

The invention will be described in detail hereinafter with reference to the drawings. Therein:

FIG. 2 shows a part of the device shown in FIG. 1,
FIGS. 6a and 6b show alternating shapes of the laminations of the collimator shown in FIG. 2, each of which is particularly suitable for the fourth embodiment.

DETAILED DESCRIPTION OF THE PREFERRED EMBODIMENT

Figure 1:
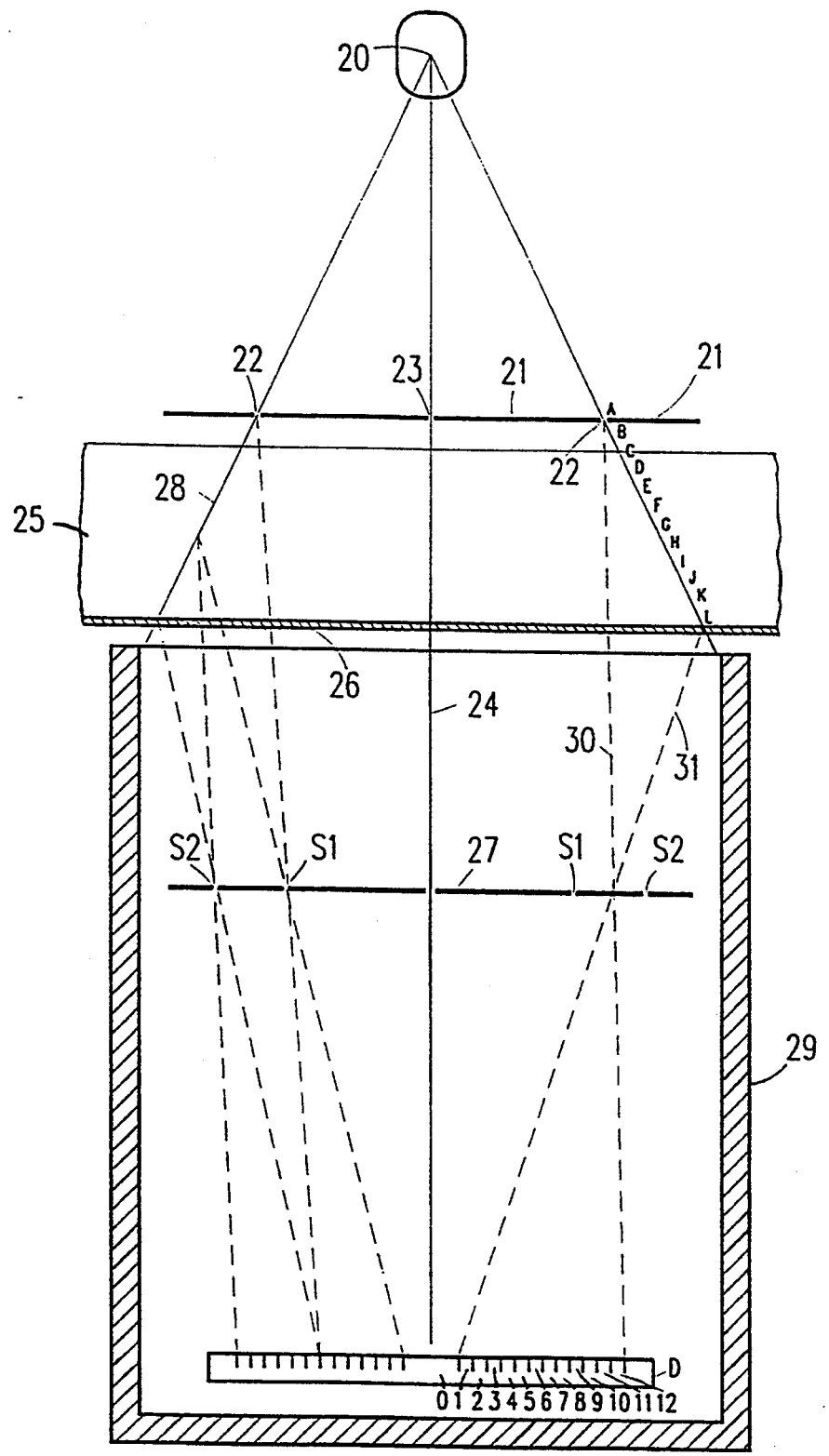
FIG. 1 shows a first embodiment of the invention.
Figure 3:
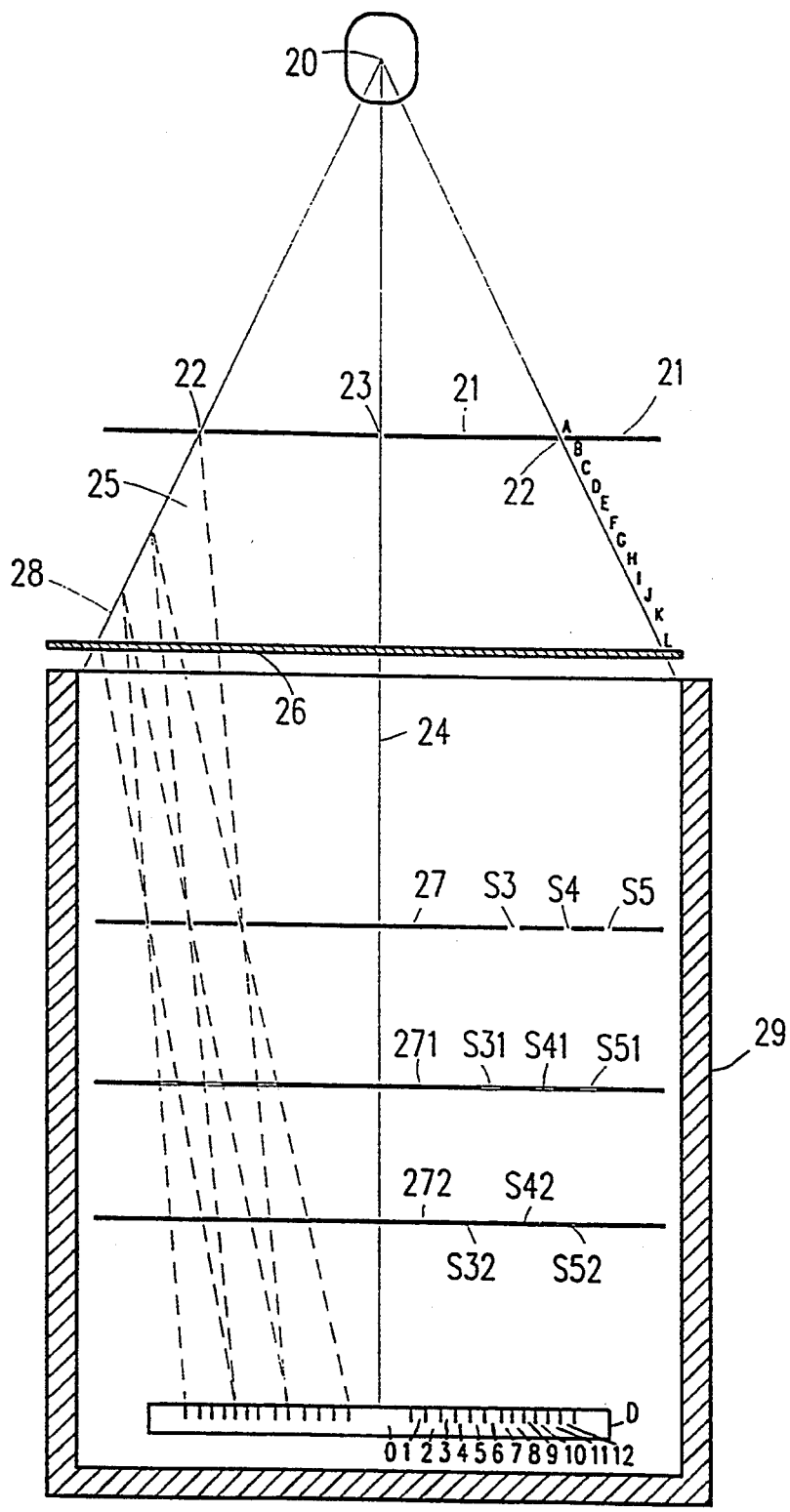
FIG. 3 shows a second embodiment of the invention.
Figure 5:
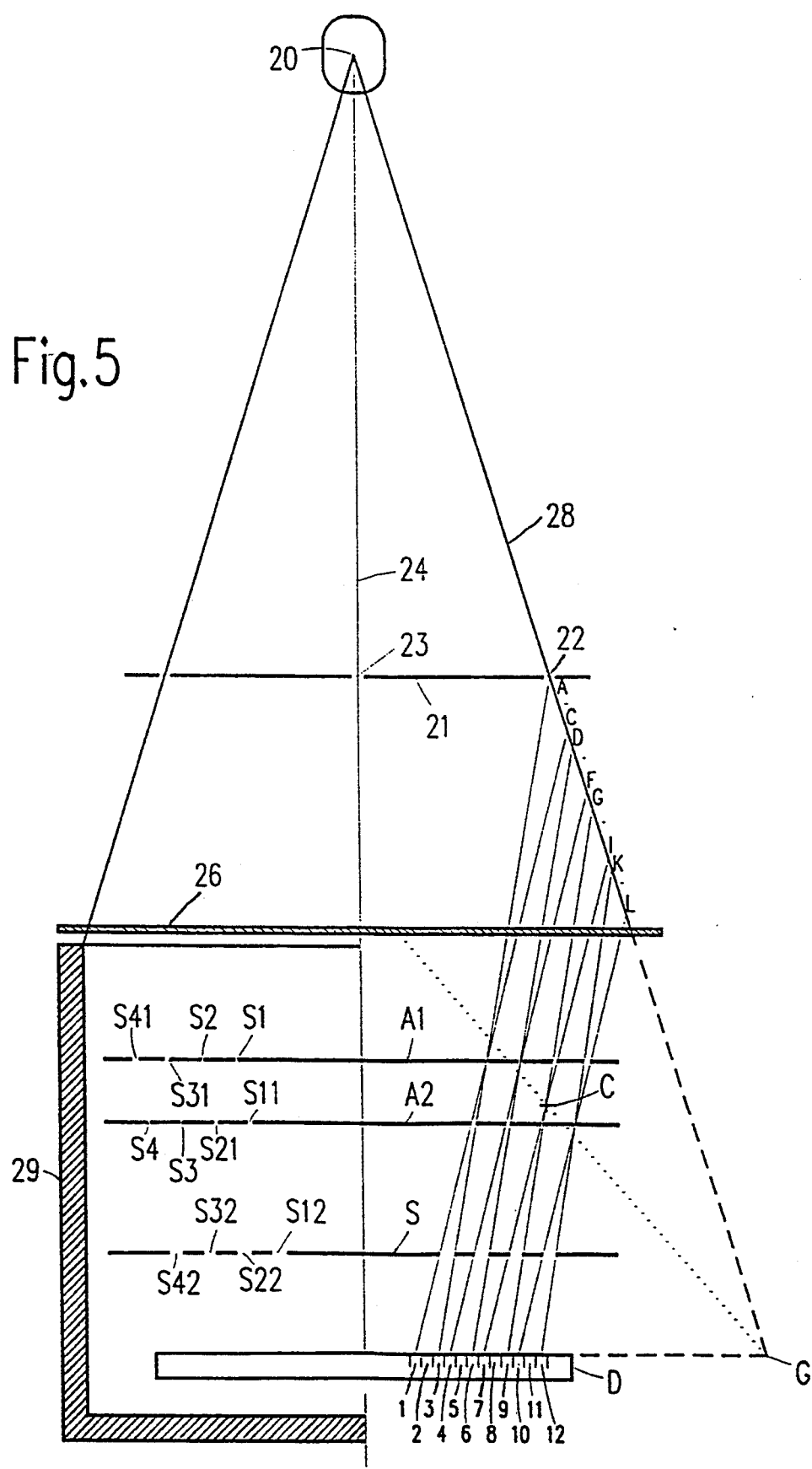
FIG. 5 is a diagrammatic view of a fourth embodiment.

The embodiments shown in the FIGS. 1, 3 and 5 are not shown to scale. The dimensions in the horizontal direction have been increased by a factor of approximately 10 in comparison with the dimensions in the vertical direction.

The reference numeral 20 denotes a polychromatic X-ray source, preferably an X-ray tube comprising an anode in the focus of which polychromatic X-rays (Bremsstrahlung) are generated by electron bombardment. For a tube voltage of, for example 150 kV, such an X-ray tube is capable of emitting X-ray quanta at least in the energy range between approximately 35 keV and 100 keV. An approximately "white" bremsstrahlung spectrum (without the characteristic lines of the K-edges) can be obtained by means of a molybdenum anode which combines a low K-edge (approximately 20 keV) and a high melting point (approximately 2600°).

The X-rays are incident on a plate 21 which is made of such a material and which has such a thickness that it is capable of absorbing the X-rays substantially completely. However, the plate 21 is provided with a circular slit 22, so that beyond the plate 21 a primary beam (28) is formed having the shape of the surface of a truncated cone. The plate 21 will be referred to hereinafter as the primary diaphragm device because it defines the primary beam. Half the angle of aperture of the primary beam amounts to 0.041 rad, for a distance of 744 mm between the source 20 and the diaphragm 21.

The primary diaphragm device 21 also comprises an aperture 23 which is situated at the centre of the circular slit 22 and which thus forms a central ray 24 which also traverses the examination zone and which constitutes the symmetry axis of the device. Therefore, in the present case the symmetry axis and the system axis are identical and the central ray is coincident with these axes. The examination zone in which the object 25 to be examined is arranged, for example a suitcase, is bounded by the diaphragm plate 21 and an X-ray transparent plate 26 which extends parallel thereto and is situated further from the focus 20 than the plate 21, for example at a distance of 450 mm from said plate 21.

The object 25 and the examination device comprising the X-ray source 20 can be shifted relative to one another in two directions perpendicular to the central ray 24, so that the entire object 25 can be successively examined by a meander-like scanning motion.

For the detection of the scattered radiation produced in the object by the primary beam 28 there is provided a detector device D which comprises a number of annular detector elements which are concentric with the axis 24 and which are suitable for energy-resolved measurement of the X-ray quanta incident thereon. The entrance plane of the detector device is situated at a distance of 2744 mm from the focus. The detector device consists of twelve annular detector elements which are concentric with the axis 24. The inner radius of the inner detector element amounts to 5.465 mm and the outer radius of the outer detector element amounts to 34.693 min.

Considering these geometrical relationships, only the scattered radiation emanating from the primary beam at a scatter angle of less than 4° can reach the detector device D. In this scatter angle range the scattered radiation is essentially elastic scattered radiation for which it is known that its wavelength does not change during the scattering process (as opposed to Compton scattered radiation). The pulse transfer spectrum of elastically scattered X-rays characterizes the (crystalline) structure of the body in which the scattering process takes place. Therefore, given substances within the object 25 to be examined can be identified in the basis of their pulse transfer spectrum. Given substances, for example explosives, can thus be identified inside a piece of luggage.

The detector device D is arranged within a tubular housing 29 which comprises a bottom plate and which is capable of absorbing the entire primary radiation traversing the boundary plate 26 and not reaching the detector device D. Inside the housing there is also provided a secondary diaphragm device 27 which consists of a flat, circular plate of a material absorbing the X-rays. The plane of the diaphragm plate is arranged at a distance of 1774.65 mm from the focus; it is situated at the point of intersection of the edge rays 30 and 31 which connect the inner edge of the primary beam 28 in the examination zone to the outer edge of the detector device or the outer edge of the primary radiation beam to the inner edge of the detector device. This position of the diaphragm plate is referred to as the 1:1 position, because the entire primary radiation beam in the examination zone could be imaged on the detector device D through an aperture in the plate 27 at the area of the point of intersection.

Said point of intersection of the edge rays 30 and 31 and the detector elements 1 . . . 12 define twelve primary beam segments A . . . L, proceeding from the inside to the outside. This is because, if an aperture were provided in the diaphragm plate at the area of the point of intersection, the detector elements 1, 2, . . . 11, 12 would receive scattered radiation from the segments L, K . . . B, A. The primary beam segments are thus associated with a respective detector element. The dimensions of these segments, in the direction of the axis 24, decrease from the inside to the outside when the detector elements are proportioned as described hereinafter.

However, the diaphragm plate is not provided with an aperture at said point of intersection, but instead comprises two slit-shaped apertures $S_1$ and $S_2$ which are shaped as rings concentric with the axis 24. The slits $S_1$, $S_2$ have radii of 25.60 mm and 38.67 mm, respectively, and a width of approximately 0.5 mm. Via the two slits, the part of the examination zone consisting of the segments A . . . F and situated nearer to the X-ray source is imaged on the inner detector elements 1 . . . 6, the remaining, outer part of the examination zone which is situated further from the X-ray source 20 and which consists of the segments G to L being imaged on the remaining detector elements 7 . . . 12. Imaging is performed so that the detector elements 1, 2 . . . 6 detect scattered radiation from the segments F, E, . . . A via the imaging slit $S_1$, whereas the detector elements 7, 8 . . . 12 detect scattered radiation from the segments L, K, . . . G via the second imaging slit $S_2$.

The dimensions of the detector elements can in principle be chosen as desired, for example so that all detector elements have the same width. However, the inner radii $r_i$ and the outer radii $r_a$ of the detector elements are chosen as follows:

$$R_i(n) = R - R_0 \cdot exp(((n_0-n) \times p + b_i)/R_0) \quad (1)$$

$$r_a(n) = R - R_0 \cdot exp(((n_0-n) \times p + b_a)/R_0) \quad (2)$$

The value R represents the radius of the circle at which the primary beam 28 would intersect the entrance plane of the detector. Using the previously stated values in respect of the distance between the detector D and the focus 20 and the angle of aperture, a value of 112.5 mm is calculated for R. For n the number of the detector element, counted from the inside to the outside, is to be inserted; in the example, n ranges from 1 to 12. $n_0$ is an integer, preferably between 1 and 12; in the present case $n_0=6$ was used. $R_o$ is the difference between the radius R and the radius on which the detector element $n_o$ should be situated. A suitable value for $R_o$ (for $n_o=6$) is 92.5 min. The values $b_i$ and $b_a$ indicate how far the inner edge and the outer edge, respectively, of the detector element $n_o$ should be situated from the circle having the radius $R-R_o$. In the present example, $b_i$ and $b_a$ are both 1 mm. The value p should be greater than the sum of $b_i$ and $b_a$. The greater this value is chosen to be relative to the sum, the greater the gap between the neighbouring detector elements will be. In the present example, p=2.5 mm was chosen.

It can be demonstrated that the width of the detector elements thus calculated (as well as the gap between neighbouring detector elements) increases in proportion to the difference between the radius R and the radius (measured at the centre) of the relevant detector element. Furthermore, the radial angular accuracy (i.e. the width of a detector element divided by the distance travelled by a scattered X-ray quantum from the primary beam to this detector element) is constant, which may be advantageous for many applications.

The output signals of the detector elements can be processed as described in the cited publications, as well as notably in the German Patent Application P4101544.4. Processing, therefore, need not be elaborated again. It is merely to be noted that for each detector element (including the detector element at the centre which detects the central ray 24) there is provided a processing channel in which the signal is amplified, digitized and applied to a pulse height analyser which records the number of X-ray quanta in the various energy ranges. For each detector element and for each energy range this number is divided by the number of X-ray quanta recorded for the relevant energy range by means of the central detector element 0. For each detector element there the energy spectrum is thus obtained, that is to say independent of the energy distribution of the X-ray quanta emitted by the X-ray source 20 and substantially independent of the attenuation of the scattered radiation by the object 25. Because the pulse transfer of an elastically scattered X-ray quantum is proportional to the product of its energy and the sine of half the scatter angle and because the scatter angle at which a given detector element receives scattered radiation from the associated segment of the primary beam is known, the pulse transfer spectra for the segments A ... L, associated with the relevant detector elements, can be calculated from the energy spectra obtained by means of the various detector elements.

An advantage of the invention over the device according to EP-OS 462 658 resides in the fact that the scatter angle at which the detector elements 1 ... 12 can receive scattered radiation from the primary beam deviate only comparatively little. The ratio of the maximum scatter angle to the minimum scatter angle amounts to only approximately 1.37. This means that the maximum quantum energy measured by the detector device need only be approximately three times greater than the minimum quantum energy (this factor is 4 in the known device) when in all segments a pulse transfer range is to be detected whose maximum value is 2.25 times greater than its minimum value. Instead of a quantum energy range of from 30 keV to 120 keV as in the present state of the art, a range of from 32 keV to 99 keV would then suffice.

In order to enable an as accurate as possible determination of the pulse transfer spectrum, the scatter angle enclosed by the scattered radiation detected by a detector element relative to the primary beam should be defined as accurately as possible. Therefore, there should only be detected scattered radiation where the scattered ray extends in the plane defined by the primary beam causing the scattered ray and the central ray 24, or at least in a sector-shaped area around this plane.

In order to suppress the other scattered radiation, there is provided a two-part collimator. For the sake of simplicity, this collimator is omitted in FIG. 1 and is shown in a plan view in FIG. 2. The collimator is symmetrically constructed relative to the axis 24 and consists of a first part which includes a tube 35 of a material which strongly absorbs the X-rays; the central ray 24 can traverse said tube 35 which also comprises radially extending laminations 36 which are uniformly distributed on its outer circumference. The second part of the collimator comprises a tube 37 of a material which strongly absorbs X-rays and which encloses the laminations 36, which tube 37 comprises laminations 33 and 34 which face inwards and which are periodically offset over its circumference. All laminations are situated in planes intersecting the system axis 24.

After its manufacture, the first part is slid into the second part, the second part preferably comprising grooves (not shown) for the laminations, so that the two collimator parts occupy a defined position relative to one another. The collimator may be subdivided in the longitudinal direction so that a first part is arranged between the plates 26 and 27 and a second part is arranged between the plates 27 and the detector device D.

FIG. 3 shows an embodiment of the invention which enables an even greater reduction of the energy range of the X-ray quanta required for a given pulse transfer range.

The diaphragm plate, again occupying the 1:1 position (at a distance of 1744.65 mm from the focus) described with reference to FIG. 1, comprises three annular imaging slits $S_3$, $S_4$ and $S_5$ which are concentric with the axis 24. Scattered radiation from the part of the examination zone formed by the inner segments A ... D of the primary beam is detected by the detector elements 1 ... 4 through the inner imaging slit $S_3$ (having a radius of 22.98 mm), i.e. so that the element 1 "perceives" the segment D and the element 4 perceives the segment A. A central part of the examination zone is imaged on a second group, consisting of the detector elements 5 ... 8, through the central imaging slit $S_4$ (having a radius of 32.66 mm). The element 5 then detects scattered radiation from the segment H and the element 8 detects scattered radiation from the segment E. Finally, via the outer imaging slit $S_5$ (having a radius of 40.46 mm), scattered radiation from the outer part of the examination zone, comprising the segments I to L, reaches the elements 9–12, the detector element 9 "perceiving" the segment L and the detector element 12 "perceiving" the segment I.

If only the diaphragm plate 27 were present, scattered radiation from the lower part (I–L) of the examination zone would inevitably reach the inner detector group (1–4) through the central slit $S_4$, or scattered radiation from the inner part (A–D) of the examination zone would inevitably be incident on the outer group (9–12) of detector elements, again through $S_4$. This undesirable scattered radiation could be eliminated by means of two mutually concentric collimator bodies shaped as the surface of truncated cones, which bodies would shield the inner and the outer group, respectively, from the undesired scattered radiation. However, from a construction point of view these shielding means would hardly be compatible with the collimator of FIG. 2 which is also required for the device shown in FIG. 3.

Therefore, at a distance of 2100 mm and 2410 mm from the focus 20 there are provided two further diaphragm plates 271 and 272, respectively, each of which comprises three annular slits $S_{31}$, $S_{41}$ and $S_{51}$ and $S_{32}$, $S_{42}$ and $S_{52}$ respectively, which are concentric with the axis 24. The width of these slits is proportioned so that the scattered radiation (for example, from the zone E–H) can reach, via the associated slit ($S_4$) in the secondary diaphragm 27, the associated group (5–8) of detector elements without obstruction, but that scattered radiation from other zones is suppressed on its way through this slit to another group of detector elements. The slits $S_{31}$ ... $S_{51}$ and $S_{32}$ ... $S_{52}$ select the scattered radiation from a given part of the examination zone. Therefore, hereinafter they are also referred to as selection slits. The width of the selection slits is greater than that of the associated imaging slits.

In the device shown in FIG. 3, the collimator body 33 ... 37 must be subdivided into several parts, one of which is situated between the examination zone and the diaphragm plate 27 whereas a further part is arranged between the diaphragm plate 27 and the plate 271, a third part being arranged between the plates 271,272 and a fourth part between the plate 272 and the detector device D.

The advantage of the device shown in FIG. 3 over that shown in FIG. 1 resides in the fact that the scatter angle range is even further reduced, so that the quotient of the maximum and the minimum scatter angle amounts to only approximately 1.2, requiring an energy range of the X-ray quanta of approximately 2.7:1 for a pulse transfer range of 2.25:1 to be detected in all segments, so that the X-ray quanta only require an energy in the range of from approximately 36 keV to 100 keV. On the other hand, as opposed to the device shown in FIG. 1, means such as the diaphragms 271 and 272 are required to shield the detector elements from scattered radiation originating from the part of the examination zone which is not associated with these detector elements.

In the device shown in FIG. 1, such shielding means can be dispensed with: scattered radiation from the inner part (A to F) of the examination zone which traverses the outer slit $S_2$, is incident outside the outer detector element 12. Scattered radiation from the outer segment (F ... L) which traverses the inner slit $S_1$, is incident on the inner part of the collimator body 35 (see FIG. 2) and is absorbed thereby.

It will be evident that the scatter angle range and hence the energy range of the X-ray quanta required for a given pulse transfer range can be further reduced when, in the same position of the diaphragm plate 27, more than three slits are provided therein so that through each slit each time one group of detector elements can detect scattered radiation from a part of the examination zone. The parts covered via different slits should be adjacent, but may not overlap. The method of determining the position of the diaphragm 27 and the radii of the imaging slits, regardless of whether they satisfy the equations (1) or (2) or not, will be described hereinafter on the basis of the following example (for four imaging slits) which is not shown in the drawings.

A first straight line is drawn from the inner edge of the segment A to the outer edge of the detector element 12 and a second straight line is drawn from the outer edge of the outer segment L to the interior of the detector element 1, it being necessary for the two lines to be situated in the same plane as the system axis 24. The point of intersection of these two lines (30 and 31 in FIG. 1) then defines the plane in which the shielding diaphragm should be situated.

Furthermore, a straight line is drawn from the inner edge of the inner segment A to the outer edge of the detector element 3. The piercing point of this line (which should be situated in one plane with the system axis, like the straight lines yet to be described) through the plane of the diaphragm plate determines the position of the first (inner) slit. Next a straight line is drawn from the inner edge of the inner detector element through the slit. This line intersects the primary beam 28 at the boundary between the segments C and D. From this point of intersection a straight line is drawn to the outer edge of the detector element 6, said line piercing the plane of the diaphragm plate at the area where the second imaging slit is to be situated, etc.

This method is performed analogously for determining the position of the third and the fourth imaging slit.

Figure 4:
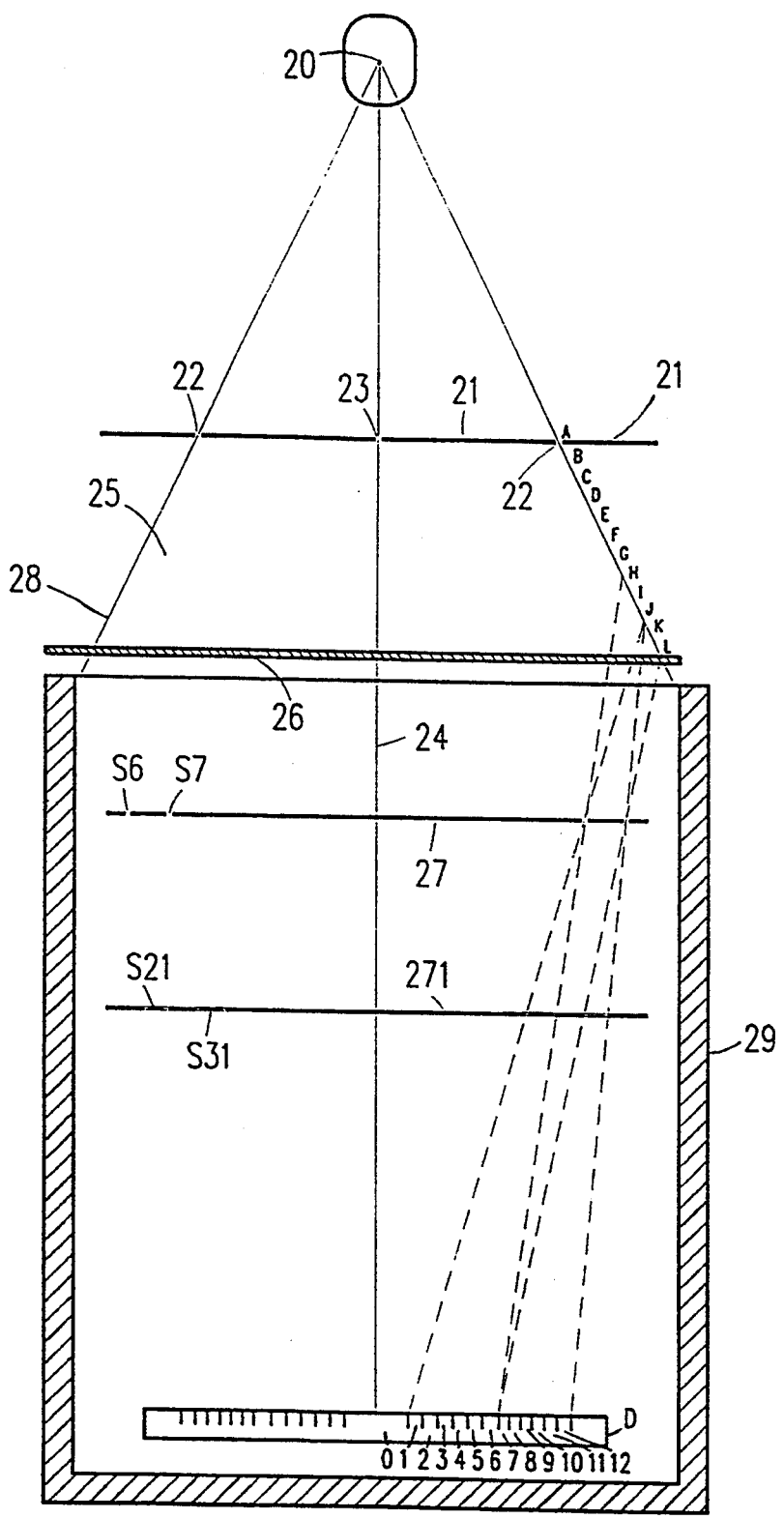
FIG. 4 shows a third embodiment of the invention.

FIG. 4 shows an embodiment of the invention which has a resolution in the direction of the system axis 24 which is higher than that of the embodiment shown in FIG. 1 or 2. The secondary diaphragm 27 is now situated in a 2:1 position, i.e. in this position through a single slit the twelve detector elements could always detect only the scattered radiation from six successive segments, for example from the segments D ... H. Each time two neighbouring detector elements would then cover a segment, the inner one of these two elements covering the outer part of the relevant segment and the outer detector element covering the inner part of this segment. In the 2:1 position the diaphragm plate 27 is situated at a distance of 1503 mm from the focus.

The plate comprises two annular slits $S_6$ and $S_7$ which are concentric with the axis 24. Through the outer slit $S_6$, having a radius amounting to 43.5 mm, the detector elements 7 ... 12 receive scattered radiation from the segments J ... L, scattered radiation from the inner part of the segment J being incident on the element 12 and scattered radiation from the outer part of the segment J being incident on the element 11; the scattered radiation from the segment L is detected by the detector elements 7 and 8.

The inner slit $S_7$ has a radius of 36.5 mm. Through this slit the elements 1 ... 12 could be struck by scattered radiation from the segments D ... I. A shielding diaphragm 271, comprising slits $S_{21}$ and $S_{31}$, however, prevents the detector elements 7 ... 12 from being struck by scattered radiation (from the segments D ... F) through the slit $S_7$. Thus, with each detector element there is associated only a single partial segment of the primary beam, the partial segments not overlapping one another and constituting a coherent part of the examination zone. It will be apparent that the scatter angles at which the detector elements can receive scattered radiation vary only comparatively little, so that the ratio of the maximum quantum energy to the minimum quantum energy need again be only slightly larger than the ratio of the maximum pulse transfer to the minimum pulse transfer to be detected within the partial segments.

In the device shown in FIG. 4 it would also be possible to provide a third slit wherethrough scattered radiation from the segments A ... C would strike the detector elements 6 ... 1. If the shielding diaphragm 271 were omitted in that case, the entire examination zone A ... L would be covered by the detector elements, i.e. so that each detector element would perceive two different sub-segments (for example, the detector 12 would perceive the inner sub-segment of D and of J). The evaluation thus becomes more difficult, but remains possible, as explained in detail with reference to FIG. 5 in European Patent Application 462 658.

The description of 2:1 imaging given with reference to FIG. 4 also holds for 3:1 or 4:1 imaging. This position is situated even nearer to the examination zone as the 2:1 position according to FIG. 4 (for a 3:1 position, the distance from the focus amounts to only 1381.9 mm). In the case of 3:1 imaging, each time six detector elements can "perceive" two segments. When each of the detector elements is struck only by scattered radiation from a single sub-segment, the shielding means for suppressing scattered radiation passing through the "wrong" slit require a complex construction. However, when it is tolerated that the detector elements detect the scattered radiation from more than one sub-segment (from three sub-segments in the case of 3:1 imaging and from four sub-segments in the case of 4:1 imaging, etc), the evaluation will be more complex because each detector element is exposed to more sub-segments which, moreover, are situated nearer one another.

The described embodiments can be combined. To this end, different secondary diaphragm devices could be present, each time one device being moved into the beam path. However, as described in detail in EP-OS 462 658, there could also be provided a diaphragm plate comprising a number of slits, each time a part of which remains unexposed whereas the remainder is covered, said diaphragm plate also being displaceable in the axial direction.

The embodiments shown in the FIGS. 1, 3 and 4 represent an optimum in as far as the secondary diaphragm device comprising the imaging slits can be formed by a flat diaphragm plate. However, these devices are unattractive in as far as on the one hand the (mean) diameter of the primary beam 28 in the examination zone is comparatively small and on the other hand the distance between the X-ray source and the detector plane is comparatively large. This large distance implies rooms with a comparatively high ceiling when examinations are performed with a vertical beam path. The comparatively small diameter of the primary beam cone in the examination zone makes it necessary to scan a piece of luggage more often, a two-dimensional relative shift then taking place between the piece of luggage and the beam path in order to ensure complete examination of the piece of luggage. The examination times are thus prolonged.

FIG. 5 shows an embodiment which is optimum in this respect, i.e. in this embodiment the distance between the X-ray source and the detector plane is smaller and at the same time the diameter of the primary radiation cone in the examination zone is greater.

FIG. 5 is drawn so that the examination device is shown to the left of the system axis (at a reduced scale in the longitudinal direction of the system axis 24), whereas some parts have been omitted to the right of the system axis 24 and instead auxiliary lines of the device are shown. Because the examination device, however, is constructed so as to be rotationally symmetrical relative to the system axis 24, the actual construction will be evident to those skilled in the art.

The device shown in FIG. 5 corresponds substantially to those shown in the FIGS. 1, 3 and 4, so that mostly the same references are used. However, this embodiment is proportioned differently, implying modifications for some of its components.

A striking aspect is that the examination zone, that is to say the plates 21 and 26, is situated substantially further from the source 20 than in the FIGS. 1, 3 and 4. The plate 21 is situated at a distance of 1187 mm from the source 20, whereas the distance between the diaphragm plate 26 and the source is 500 mm greater.

For such a large distance between the examination zone and the source the primary beam 28, irradiating the examination zone, cannot simply have the same angle of aperture as in the embodiments shown in the FIGS. 1, 3 and 4. This is because otherwise either the distance between the detector device and the source 20 would be further increased (which is undesirable) or the outer diameter of the detector device would be further increased (suitable germanium detectors, however, at present are available only with a maximum outer diameter of approximately 70 mm), or the mean scatter angle at which the detector device receives scattered radiation from the examination zone would have to be increased. The latter would require the detection of X-ray quanta of lower energy for the same pulse transfer spectrum, said energy, however, being substantially absorbed by a piece of luggage in the examination zone.

The (half) angle of aperture of the primary beam therefore, amounts to only 0.0309 rad. Nevertheless, because of the greater distance between the examination zone and the source, the dimensions of the primary beam cone in the examination zone are greater than in the other embodiments.

It can be demonstrated that, using a detector device having an outer diameter of 70 mm, the energy can be received from the examination zone at a mean scatter angle of 0.052 rad (approximately 3°) in the case of a distance of 2500 mm between the detector plane and the source. The distance between the plate 26 and the detector plane then amounts to only approximately 813 mm (this distance amounts to 1550 mm in the embodiments shown in the FIGS. 1, 3 and 4). At this comparatively small distance between the examination zone and the detector plane some disturbing effects occur which can still be tolerated in the embodiments shown in the FIGS. 1, 3 and 4.

One of the disturbing effects caused by the small distance between the detector plane and the examination zone consists in that the angle between the lines 30 and 31 (FIG. 1), connecting the inner edge of the examination zone to the outer edge of the detector device and the outer edge of the examination zone to the inner edge of the detector device, respectively, becomes increasingly greater. This difference in scatter angle can be reduced in conformity with the FIGS. 1, 3 or 4 by providing even more imaging slits in the diaphragm plate 27, but this number of slits cannot be increased arbitrarily because it will then become increasingly more difficult to shield detector elements from scattered radiation from the parts of the examination zone with which they are not associated.

In FIG. 5 a different approach is followed in as far as the imaging slits are no longer provided in one plane but so that a constant imaging scale is obtained (the imaging scale is the ratio of the distances travelled by a scattered X-ray quantum before and after the imaging slit). A constant imaging scale is obtained when the imaging slits are situated on the external surfaces of a cone which is concentric with the system axis 24 and which intersects the detector plane in the same circle as that in which the primary beam 28 would intersect the detector plane. In the right half of FIG. 5 the external surface of the cone is denoted by a dashed line interconnecting the points G and C. The point G is situated on the intersecting line of the primary beam 28 and the detector plane, whereas the point C is defined by the edge rays 30 and 31 (see FIG. 1).

When the imaging slits are situated on this surface of cone, the subdivision of the detector device is arbitrary: it is reproduced on the primary beam. Preferably, such a subdivision is chosen that all detector elements have the same width. According to this subdivision, substantially all detector elements would supply signals of the same magnitude if the examination zone were filled with a homogeneous body.

In the case of a constant detector width, the mean radius r of a detector element satisfies:

$$r = R_1 + (n - 0.5) \cdot B/n_1$$

Therein, $R_1$ is the inner radius of the inner detector element and B is the width of the detector device (difference between the outer radius of the outer detector element and the inner radius of the inner detector element). n is again the number of the detector elements, counting from the inside towards the outside, and $n_1$ is the number of detector elements. In the present embodiment, $R_1 = 9$ mm, $B = 26$ mm, and $n_1 = 12$.

Because of the small distance between the examination zone and the detector plane, it is advisable to provide four imaging slits on said surface of cone, the inner slit being associated with the detector elements 1 to 3 the next slit with the detector elements 4 to 6, the next slit with the detector elements 7 to 9, and the outer slit with the detector elements 10 to 12. Each of these four groups of detector elements perceives a part of the examination zone whose depth (dimension in the direction of the system axis 24) corresponds to one quarter of the depth of the examination zone.

The position of the slits on the surface of cone is obtained when straight lines are drawn from the centre of the central detector element of each group, i.e. from the centre of the detector elements 2, 5, 8 and 11, which straight lines intersect, the primary beam 28 at the mean scatter angle of 0.052 rad in a plane containing the system axis 24. The point of intersection of these straight lines with the dotted straight line defines the position and the radius of the four imaging slits.

In order to realise the four imaging slits in practice, either in appropriate positions four flat diaphragm plates should be provided with appropriate imaging slits which are concentric with the system axis 24, or there should be provided a rotationally symmetrical diaphragm body of complex shape and comprising four imaging slits. Both solutions are comparatively intricate.

FIG. 5 shows a simpler solution, involving only two flat diaphragm plates A1 and A2. The diaphragm plate A1 is situated halfway between the two planes in which the two inner imaging slits should be situated in the ideal case, and the diaphragm plate A2 is situated halfway between the two planes in which the two outer slits should be situated when the imaging scale is to be identical for all imaging slits. The radii of the slits in these two planes are chosen so that said straight lines extend from the centre of the detector elements 2, 5, 8 and 11 through these imaging slits. The diaphragm plate A1 is situated at a distance of 1915 mm from the radiation source 20, whereas the diaphragm plate A2 is situated at a distance of 2039 from the source. The radii of the two imaging slits $S_1$ and $S_2$ in the diaphragm plate A1 amount to 24.74 and 31.26 mm, respectively, whereas the radii of the imaging slits $S_3$ and $S_4$ in the diaphragm plate A2 amount to 35.17 and 41.70 mm, respectively.

Via the slit $S_1$, the detector elements 1 to 3 should cover the inner (upper) part of the examination zone (A ... C), whereas the subsequent part of the examination zone (D ... F) is imaged via the imaging slit $S_2$, on the detector elements 4 to 7. Via the imaging slit $S_4$, the detector elements 10 ... 12 "perceive" the part (J ... L) of the examination zone which is situated furthest away (at the bottom), whereas the adjoining part (G ... I) is imaged on the detector elements 7 to 9 via the slit $S_3$.

In order to prevent scattered radiation from a neighbouring part of the examination zone from being incident on a group of detector elements via a neighbouring slit, as in the embodiment shown in the FIGS. 3 and 4 there should be provided selection slits so that each group of detector elements can receive scattered radiation from the examination zone only via its associated imaging slit. These selection slits are provided each time in the other diaphragm plate. For example, the selection slit provided to ensure that the detector elements 1 to 3 receive scattered radiation only via the selection slit $S_1$ in the diaphragm plate A1, should be provided in the diaphragm plate A2. Similarly, the selection slit $S_{21}$ for the detector elements 4 to 6 is provided in the diaphragm plate A2, whereas the selection slits $S_{31}$ and $S_{41}$, intended to ensure that the detector elements 7 to 9 and 10 to 12 receive scattered radiation only via the slits $S_3$ and $S_4$, respectively, in the diaphragm plate A2, are provided in the diaphragm plate A1.

The selection slits $S_{11} \ldots S_{41}$ have radii of 22.05 mm, 28.6 mm, 37.9 mm and 44.45 mm, respectively. Their width increases from the inside to the outside from 1.9 mm to 2.5 mm.

The selection slits $S_{11} \ldots S_{41}$ are not yet adequate to shield the detector elements $1, 2, 3, \ldots, 10, 11, 12$ against scattered radiation from non-associated parts of the examination zone. Therefore, a further diaphragm plate S, being situated at a distance of 2300 mm from the source 20, is provided with further selection slits $S_{12} \ldots S_{42}$. The centre lines of these selection slits have a radius of 16.4 mm, 23.0 mm, 29.5 mm and 36 mm, respectively. The width of these slits decreases from the inside to the outside from 4.2 mm to 3.6 mm.

As has already been described with reference to the FIGS. 1 and 2, scattered X-ray quanta which intersect the plane defined by the generating primary beam and the system axis at a comparatively large angle should not be detected by the detector device, because otherwise the scatter angle range covered by the individual detector elements would be increased. Therefore, in the embodiment shown in FIG. 5 it is also necessary to provide a collimator with laminations in the area between the plate 26 and the detector plane, preferably in each of the four segments defined by the diaphragm plates A1, A2 and S, said laminations being situated in planes containing the system axis 24.

If all laminations of the collimator of FIG. 2 were to have the same length and the same width, the detector elements situated further outwards could receive scattered radiation from a larger scatter angle range than the inner detector elements.

For the parts of the examination zone associated with the outer detection elements, therefore, the pulse transfer could not be determined with the same accuracy as for the other parts. In order to avoid this situation, the laminations of the collimator shown in FIG. 2 are of a different width. They are arranged so that the clearance between the laminations varies as little as possible as a function of the distance from the system axis.

However, when this clearance, or the variation of the scatter angle each time possible, is considered as a function of the distance from the system axis, discontinuities occur for the distances where new laminations are added. These discontinuities are more disturbing as the collimator is shorter.

Such discontinuities can be avoided when the dimensions of the laminations increase from the inside to the outside in the direction parallel to the system axis. FIG. 6c shows such a lamination. The right-hand side of the lamination 36 within the collimator of FIG. 2 neighbours the system axis. The upper right-hand corner is oblique.

FIG. 6b shows a different shape of the lamination 36, the upper and the lower corner being oblique. All feasible shapes of this lamination have a common aspect in that their dimensions parallel to the system axis are the same as a function of the distance from the system axis. It is also possible to combine the two solutions (different widths of the laminations in conformity with FIG. 2 and dimensions increasing from the inside to the outside in conformity with the FIGS. 6a–6b). In that case the laminations 33 and 34 should have a shape analogous to that of the lamination 36.

The above embodiments involve rotational symmetry. However, rotational symmetry is in principle not required. For example, use can also be made of a primary beam having a semi-circular cross-section when the slits in the diaphragm device and the detector elements also have a semi-circular shape. Moreover, it is not necessary for the cross-section of the primary beam, the slits and the detector elements to be circular. Generally speaking, the primary beam should propagate in the examination zone as a surface of cone (or a sector of such a surface of cone). The primary beam may be a flat fan-shaped beam as described in detail in EP-OS 462 658 with reference to the FIGS. 9 and 10. A sector on the external surface of a cone whose half angle of aperture amounts to exactly 90° leads to such a fan-shaped beam. In that case the system axis extends to the focus of the X-ray source perpendicularly to the fan-shaped beam. On the other hand, the primary beam in the examination zone becomes a pencil beam when the aperture of the cone amounts to 0°. The invention can also be used in those cases. Therefore, the term "cone" is to be broadly interpreted in the present context.

I claim:

1. A device for measuring the pulse transfer spectrum of X-ray quanta elastically scattered from an examination zone, comprising:

a polychromatic X-ray source, a primary diaphragm device which is arranged between the X-ray source and the examination zone and which serves to form a primary beam irradiating the examination zone along a surface of a cone, a detector device comprising a plurality of adjoining detector elements which are arranged for detecting X-ray quanta scattered from a corresponding plurality of associated adjoining segments of the primary beam within the examination zone at different distances from the X-ray source, said plurality of adjoining segments being grouped into a plurality of parts of the examination zone intercepted by the primary beam and said detector elements being grouped into a plurality of groups of adjoining detector elements equal to the number of said parts of the examination zone, and a secondary diaphragm device which is arranged between the examination zone and the detector device and which comprises a plurality of imaging slits, equal to both the number of groups of detector elements and the number of parts of the examination zone, each imaging slit being an arc of circle about a system axis extending from the X-ray source to the detector device, wherein the detector elements of the detector device are situated at different respective distances from the system axis and the imaging slits are arranged in the secondary diaphragm device so that via each imaging slit the quanta scattered from a different associated part of the examination zone can reach a different associated group of detector elements, the quanta scattered from a part of the examination zone which is situated nearer to the X-ray source being detected by a group of detector elements situated at smaller distances from the system axis than a group of detector elements detecting quanta scattered from a part of the examination zone which is situated farther from the X-ray source and that the quanta scattered from a segment farther from the X-ray source in a part of the examination zone is detected on a detector element of the associated group that is situated at smaller distance from the system axis than a detector element of the associated group detecting quanta scattered from a segment of the part of the examination zone which is situated nearer to the X-ray source.

2. A device as claimed in claim 1, wherein the number of imaging slits, the number of parts of the examination zone intercepted by the primary beam, and the number of groups of detectors is only two, said imaging slits are at different distances from the system axis, and that via the imaging slit which is situated at the smaller distance from the system axis the part of the examination zone intercepted by the primary beam which is situated nearer to the X-ray source is imaged on the group of detector elements situated nearer to the system axis, the other part of the examination zone being imaged on the other group of detector elements via the other imaging slit.

3. A device as claimed in claim 1, wherein the number of imaging slits, the number of parts of the examination zone intercepted by the primary beam, and the number of groups of detectors is n, where n is an integer greater than 2, and that the group of detector elements and the part of the examination zone associated therewith by an imaging slit being situated at a distance from the system axis which is greater as the radius of curvature of the associated imaging slit is greater.

4. A device as claimed in claim 1, wherein all imaging slits are provided in a single, flat diaphragm plate.

5. A device as claimed in 1, wherein the imaging slits are situated in at least two different planes, the imaging slits of smaller radius being situated nearer to the examination zone.

6. A device as claimed in 1, wherein, for the purpose of shielding, selection slits are provided between the examination zone and the detector device, the position and dimensions of said selection slits being such that the groups of detector elements are struck only by scattered radiation from their associated parts of the examination zone.

7. A device as claimed in 1, wherein the secondary diaphragm device comprises at least two flat diaphragm plates which comprise selection slits, in addition to said imaging slits, so that the scattered radiation detected by the individual detector elements traverses an imaging slit and at least one selection slit 8. A device as claimed in 1, wherein between the examination zone and the detector device there is provided a collimator device which comprises laminations for absorbing X-rays, the laminations being situated in planes containing the system axis.

9. A device as claimed in claim 8, wherein the laminations have different dimensions in the direction perpendicular to the system axis so that a clearance between the laminations varies as little as possible as a function of the distance from the system axis.

10. A device as claimed in 1, wherein at their side facing the system axis the laminations are shorter than at their side which is remote therefrom.

11. A device as claimed in 1, wherein the examination zone contains a point midway between the X-ray source and the detector device, situated nearer to a boundary of the examination zone facing the detector than a boundary of the examination zone facing the X-ray source.

12. A device as claimed in 1, wherein the secondary diaphragm device is provided in such a position between the detector device and the examination zone that each group of detector elements can detect only radiation from the associated part (G . . . L) of the examination zone, there being provided shielding means which shield each group of detector elements from radiation scattered from the parts of the examination zone not associated with the group.

* * * * *